(12) United States Patent
Mei

(10) Patent No.: US 8,357,678 B2
(45) Date of Patent: Jan. 22, 2013

(54) CHAIR RUTHENIUM COMPLEXES AND THEIR USE AS ANTICANCER AGENTS

(75) Inventor: Wenjie Mei, Guangzhou (CN)

(73) Assignee: Guangdong Pharmaceutical University, Guangdong (CN)

( * ) Notice: Subject to any disclaimer, the term of this patent is extended or adjusted under 35 U.S.C. 154(b) by 263 days.

(21) Appl. No.: 12/680,661

(22) PCT Filed: Jul. 21, 2008

(86) PCT No.: PCT/CN2008/001347
§ 371 (c)(1),
(2), (4) Date: Mar. 29, 2010

(87) PCT Pub. No.: WO2009/043223
PCT Pub. Date: Apr. 9, 2009

(65) Prior Publication Data
US 2010/0216993 A1   Aug. 26, 2010

(30) Foreign Application Priority Data
Sep. 29, 2007   (CN) .......................... 2007 1 0030650

(51) Int. Cl.
*A61K 31/555* (2006.01)
*C07F 15/00* (2006.01)

(52) U.S. Cl. .......................................... 514/185; 546/10
(58) Field of Classification Search ................... 514/185; 546/10, 2
See application file for complete search history.

(56) References Cited

OTHER PUBLICATIONS

Liu, Y.-J. et al.: Interaction of polypyridyl ruthenium (II) complex containing asymmetric ligand with DNA. J. of Inorg. Biochem., vol. 99, pp. 530-537, 2005.*

* cited by examiner

*Primary Examiner* — Charanjit Aulakh
(74) *Attorney, Agent, or Firm* — Sughrue Mion, PLLC

(57) ABSTRACT

The invention is reported a type of chair ruthenium complexes and their used as anticancer agent. The general formulae of these chair ruthenium complexes is: A-[Ru(bpy)$_2$L](PF$_6$)$_2$, where in A is Δ or Λ, L is tFPIP, IPBP, IPBH or PYNI. These chair ruthenium complexes is characterized with that the center atom is ruthenium ion, the main ligand is 2-phenyl imidazole[4,5*f*][1,10]phenanthroline and its derivate, the co-ligand is two bipyridine, and the space structure is rigid octahedral. The complexes indicated by the invention are the chair isomer of all of these ruthenium complexes. This type of ruthenium complexes exhibit excellent inhibitory activity against liver cancer cell line BEL-7402, and can be used in preparing anticancer agent.

5 Claims, No Drawings

CHAIR RUTHENIUM COMPLEXES AND THEIR USE AS ANTICANCER AGENTS

FIELD OF INVENTION

This invention pertains to the field ruthenium complexes, in particular, to the use of therapeutically active of chair ruthenium complexes in the treatment of cancer.

BACKGROUND OF INVENTION

Cancer is one of the most fatally disease to threaten human-being. The mortality rate resulted from cancer is only less to blood vessel disease in all kind of disease, and in some developed country, it's the first cause. In 90's, the incidence of a cancer is over 2,000,000 per year in china. The treatment on cancer in clinic is usually by chemotherapy, operation and irradiation.

Cisplatin have been used extensively in clinic since it has been found to have excellent antitumor activity by Rosenberg in 1969, and it has been used to treat bladder cancer, prostatic carcinoma, adenocarcinoma of lung, head and neck cancer, breast cancer, lymphoma and leukemia. However, the water solubility of cisplatin is poor and can only be administrated by injection. It's found that cisplatin exhibit heavy toxic on the kidney, the gastrointestinal tract, ear and never, and resistance to drug will occur after administrated over a long period of time.

Thus, there are more and more attentions have been focused on novel metal complexes, and its show that platinum, rhodium, germanium, and tin complexes, especially ruthenium complexes exhibit excellent antitumor activity.

CONTENT OF INVENTION

The object of the present invention is to provide a class of compound which are chair ruthenium(II) complexes that have anti-cancer activity to overcome the deficiency of existing technology.

In accordance with another aspect of the present invention, there is provided a use of a compound denoted in the preparation of an anticancer composition.

In the present invention, a series of chair ruthenium(II) complexes have been synthesized. These complexes is characterized by that: 1) the centre atom is ruthenium(II) ion, and the complex ion have a rigid octahedral space structure, 2) there are two bipyridine group as co-ligand in the complex, 3) the main ligand is 2-phenylimidazole[4,5-f][1,10]phenanthroline and its derivative, and 4) all of these ruthenium(II) complexes is charity, have isomers.

This chair ruthenium complex have a general formula A-[Ru(bpy)$_2$L](PF$_6$)$_2$, wherein, A is Δ or Λ; L is tFPIP, IPBP, IPBH or PYNI.

Compounds of present invention include, but are not limited to the following exemplary compounds:
Δ-[Ru(bpy)$_2$(tFPIP)](PF$_6$)$_2$, Λ-[Ru(bpy)$_2$(tFPIP)](PF$_6$)$_2$, Δ-[Ru(bpy)$_2$(IPBP)](PF$_6$)$_2$, Λ-[Ru(bpy)$_2$(IPBP)](PF$_6$)$_2$, Δ-[Ru(bpy)$_2$(IPBH)](PF$_6$)$_2$, Λ-[Ru(bpy)$_2$(IPBH)](PF$_6$)$_2$, Δ-[Ru(bpy)$_2$(PYNI)](PF$_6$)$_2$, Λ-[Ru(bpy)$_2$(PYNI)](PF$_6$)$_2$.

These declared chair ruthenium complexes exhibit excellent anti-tumor activity, and can be used in preparing anti-cancer agents.

Compared to present technology, the invention is precede in the designed and prepared a series of chair ruthenium complexes, and these complexes exhibit obvious inhibitory activity against the growth of liver cancer cells to be used in preparing anti-cancer agents.

PREPARATION OF COMPOUNDS

Example 1

Preparation of Δ-[Ru(bpy)$_2$(tFPIP)](PF$_6$)$_2$ (Δ-1)

The synthesis route of complex Δ-[Ru(bpy)$_2$(FPIP)](PF$_6$)$_2$ (Δ-1) is show in Figure (I):

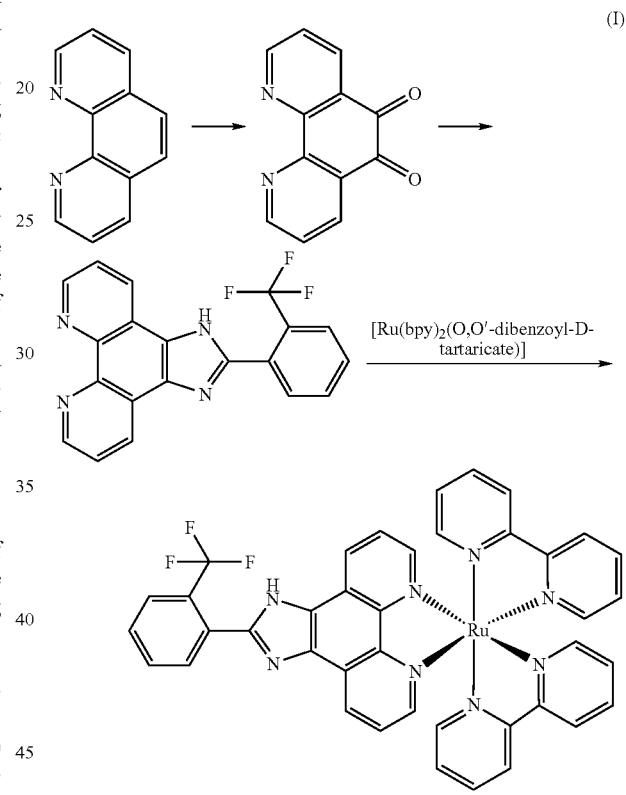

(I)

1.1 Preparation of phenanthroline dione-5,6

1,10-phenanthroline (4 g, 21.88 mmol) and KBr (4 g, 33.9 mmol) was in ice bath, and a solution compose of concentrated H$_2$SO$_4$ and concentrated HNO$_3$ was added in slowly with stir, after the reaction mixture was refluxed for 40 min, Br$_2$ was given off. Then the reaction mixture was transferred to a beaker, and the pH of solution was adjusted to 7.0 by adding 6 mol·L$^{-1}$ NaOH solution, and extracted with chloroform (100 mL) for three times. The organic phase was combined and washed with water (50 mL) for 1-2 times, and anhydrous Na$_2$SO$_4$ was added. The crude product was obtained by distilling chloroform solution under extracted pressure after stayed at room temperature overnight. The crude product was dissolved in ethanol, and purified in 60-100 mesh silicon column, re-crystal in ethanol to give yellow needle-like crystal, yield 74.8%.

1.2 Preparation of 2-(2-trifluoromethane phenyl)imidazole[4,5-f][1,10]phenanthroline (tFPIP)

Phenanthroline dione-5,6 (2.6 g, 12 mmol) and 2-trifluoromethyl benzaldehyde (2.5 g, 18 mmol), ammonium acetate (19 g, 25 mmol) and glacial acetic acid (100 ml) refluxed for 4 h with stir, and then the solution was cooled to room temperature. After distilled water was added in, the pH of the solution was adjusted to neuter, and the solution was extracted with chloroform (20 mL) for 3 times. The crude product was obtained by distilled the solution under extracted pressure and dried in vacuum. The crude was dissolved by methanol, purified by silicon column, and the yellow band was collected, concentrated and dried to give a pale-yellow solid, yield, 86.7%.

1.3 Preparation of cis-[Ru(bpy)$_2$Cl$_2$].2H$_2$O

RuCl$_3$.nH$_2$O (1.56 g, 6 mmol), bipyridine (1.87 g, 12 mmol) and LiCl (2.42 g, 57.6 mmol) was dissolved in 15 ml DMF, and refluxed for 8 h under Ar atmosphere. The reaction mixture was cooled to room temperature, acetone (50 mL) was added and stayed at frozen overnight, and dark-purple fine crystal was obtained after filtrated. The crystal was washed to pale by using distilled water and dried, yield 71.0% (calculated according to bipyridine).

1.4 Preparation of cis-[Ru(bpy)$_2$(py)$_2$]Cl$_2$ cis-[Ru(bpy)$_2$Cl$_2$].2H$_2$O (2.0 g), pyridine (23 ml) and distilled water (46 ml) was refluxed for 4 h in stir. After the solvent was removed off by distilled, methanol (46 ml) was added to dissolve the red solid, and ether (300 mL) was added. The solution was stand at room temperature for 1 h to give red-crystal, and then extracted and washed with ether, yield 84.5%.

1.5 Preparation of Δ-[Ru(bpy)$_2$(py)$_2$][O,O'-dibenzoyl-D-tartaricate].12H$_2$O cis-[Ru(bpy)$_2$(py)$_2$Cl$_2$] (1.95 g) was dissolved in distilled water (30 ml), and sodium O,O'-dibenzoyl-D-tartaricate solution (0.5M, 19.0 ml) was added under stir at room temperature, and then the solution was stirred for another 10 min. There are red crystal was obtained in a week by put the solution in ventilated fume, yield 79.3%.

1.6 Preparation of Δ-[Ru(bpy)$_2$(FPIP)](PF$_6$)$_2$ (Δ-1)

Δ-[Ru(bpy)$_2$(py)$_2$][O,O'-dibenzoyl-d-tartrate].12H$_2$O (0.13 g, 0.1 mmol) and tFPIP (0.105 g, 0.28 mmol) was dissolved in the mixture solution combined by glycol and water, and the solution was refluxed for 6 h. Then the reaction solution was cooled to room temperature, filtrated, and diluted by water (40 mL), and saturation NH$_4$PF$_6$ solution was added to give an orange precipitation. The mixture was filtrated extraction, and the precipitate was washed by water ether and dried in vacuum. The crude product was dissolved in CH$_3$CN (5 mL), purified by Al$_2$O$_3$ column using CH$_3$CN—C$_6$H$_5$CH$_3$ solution as elute, and the main red composite was collected, dried in vacuum, re-crystal from CH$_3$CN—C$_6$H$_5$CH$_3$ solution to give orange crystal, yield, 79%. ESI-MS (m/e): 777.2; 389.2. CD (in Tris-HCl, pH=7.2, $\lambda_{max}$): −291.0 nm.

Example 2

Preparation of Λ-[Ru(bpy)$_2$(tFPIP)](PF$_6$)$_2$(Λ-1)

The synthesis route of Λ-[Ru(bpy)$_2$(FPIP)](PF$_6$)$_2$ (Λ-1) was show in Figure (II):

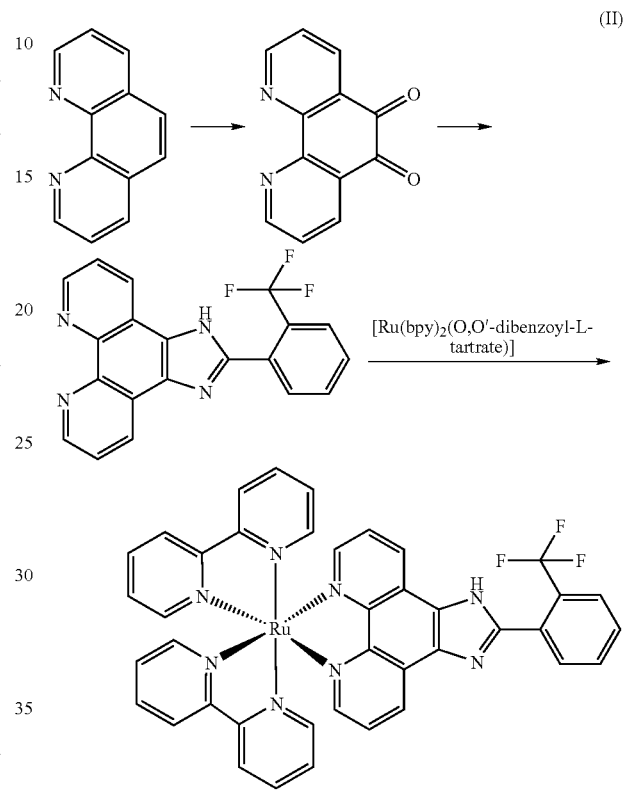

(II)

Phenanthroline dione-5,6,2-(2-trifluoromethane phenyl) imidazole [4,5-f][1,10]phenanthroline (tFPIP), cis-[Ru(bpy)$_2$Cl$_2$] and cis-[Ru(bpy)$_2$ (py)$_2$]Cl$_2$ was synthesized according the same procedure as that in example 1.

2.1 Preparation of Λ-[Ru(bpy)$_2$(py)$_2$][O,O'-dibenzoyl-L-tartaricate].12H$_2$O cis-[Ru(bpy)$_2$(py)$_2$Cl$_2$] (1.95 g) was dissolved in distilled water (30 ml), and sodium O,O'-dibenzoyl-L-tartaricate solution (0.5M, 19.0 ml) was added under stir at room temperature, and then the solution was stirred for another 10 min. There are red crystal was obtained in a week by put the solution in ventilated fume, yield, 73%.

2.2 Preparation of Λ-[Ru(bpy)$_2$(tFPIP)](PF$_6$)$_2$ (Λ-1)

Λ-[Ru(bpy)$_2$(py)$_2$][O,O'-dibenzoyl-1-tartrate].12H$_2$O (0.13 g, 0.1 mmol) and tFPIP (0.105 g, 0.28 mmol) was dissolved in the mixture solution combined by glycol and water, and the solution was refluxed for 6 h. Then the reaction solution was cooled to room temperature, filtrated, and diluted by water (40 mL), and saturation NH$_4$PF$_6$ solution was added to give an orange precipitation. The mixture was filtrated extraction, and the precipitate was washed by water ether and dried in vacuum. The crude product was dissolved in CH$_3$CN (5 mL), purified by Al$_2$O$_3$ column using CH$_3$CN—C$_6$H$_5$CH$_3$ solution as elute, and the main red composite was collected, dried in vacuum, re-crystal from CH₃CN—C₆H₅CH₃ solution to give orange crystal, yield, 76%. ESI-MS (m/e): 777.3; 389.3. CD (in Tris-HCl, pH=7.2, $\lambda_{max}$): +291.0 nm.

Example 3

Preparation of Δ-[Ru(bpy)₂(IPBP)](PF₆)₂ (Δ-2)

The synthesized route of Δ-[Ru(bpy)₂(IPBP)](PF₆)₂ (Δ-2) was show in figure (III):

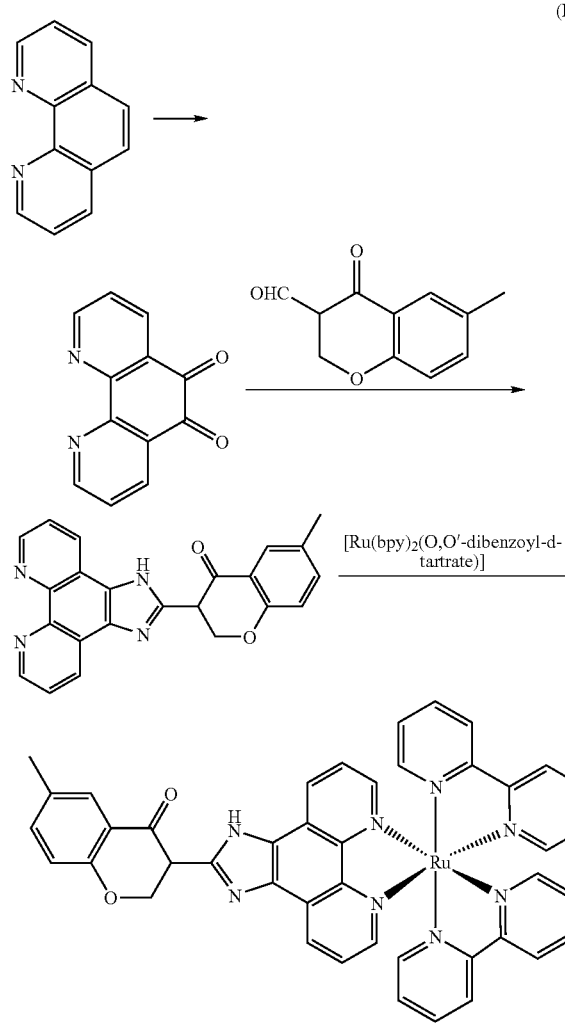

Phenanthroline dione-5,6, cis-[Ru(bpy)₂Cl₂], cis-[Ru(bpy)₂(py)₂]Cl₂ and Δ-[Ru(bpy)₂(by)₂][O,O'-dibenzoyl-d-tartrate].12H₂O was synthesized according the same procedure as that in example 1.

3.1 Preparation of 2-(4-methyl-1,2-benzopyriran-2-one)imidazole [4,5-f][1,10]phenanthroline (IPBP)

Phenanthroline dione-5,6 (0.315 g, 1.5 mmol) and chromone-3-carboxaldehyde 0.261 g (1.5 mmol), ammonium acetate (2.31 g, 30 mmol) and glacial acetic acid (20 ml) refluxed for 2 h with stir, cooled to room temperature and diluted by water (80 mL). Then the pH of the solution was adjusted to nearly neuter, and the solution was extracted with chloroform (20 mL) for 3 times. The crude product was obtained by distilled the solution under extracted pressure and dried in vacuum. The crude was dissolved by methanol, purified by silicon column, and the yellow band was collected, concentrated and dried to give a pale-yellow solid, yield, 73%.

3.2 Preparation of Δ-[Ru(bpy)₂(IPBP)](PF₆)₂ (Δ-2)

Δ-[Ru(bpy)₂(py)₂][O,O'-dibenzoyl-d-tartrate].12H₂O (0.26 g, 0.2 mmol), and IPBP (0.210 g, 0.56 mmol) was dissolved in the mixture solution combined by glycol and water, and the solution was refluxed for 6 h. Then the reaction solution was cooled to room temperature, filtrated, and diluted by water (40 mL), and saturation NH₄PF₆ solution was added to give an orange precipitation. The mixture was filtrated extraction, and the precipitate was washed by water ether and dried in vacuum. The crude product was dissolved in CH₃CN (5 mL), purified by Al₂O₃ column using CH₃CN—C₆H₅CH₃ solution as elute, and the main red composite was collected, dried in vacuum, re-crystal from CH₃CN—C₆H₅CH₃ solution to give red crystal, yield, 70%. ESI-MS (m/e): 791.3. CD (in Tris-HCl, pH=7.2, $\lambda_{max}$): −291.0 nm.

Example 4

Preparation of Λ-[Ru(bpy)₂(IPBP)](PF₆)₂ (Λ-2)

The synthesized route of Λ-[Ru(bpy)₂(IPBP)](PF₆)₂ (Λ-2) was show in figure (IV).

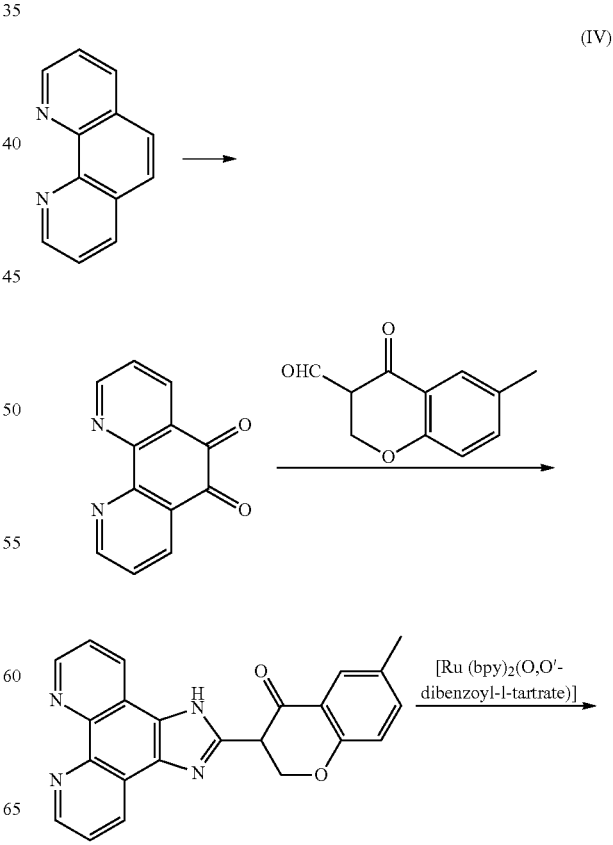

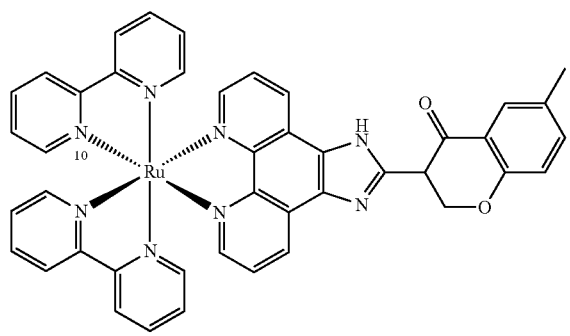

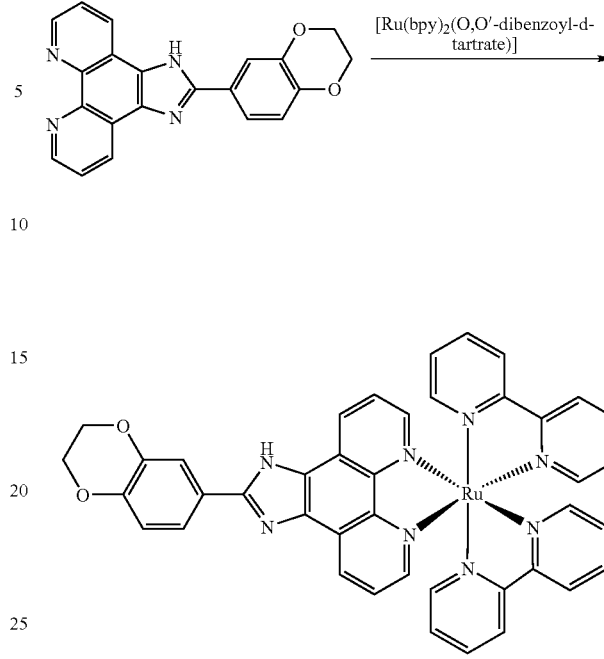

Phenanthroline dione-5,6, cis-[Ru(bpy)₂Cl₂] and cis-[Ru(bpy)₂(py)₂]Cl₂ was synthesized according the same procedure as that in example 1. [Ru(bpy)₂(py)₂][O,O'-dibenzoyl-1-tartrate].12H₂O was synthesized according the same procedure as that in example 2. IPBP was synthesized according the same procedure as that in example 3.

Λ-[Ru(bpy)₂(bpy)₂][O,O'-dibenzoyl-1-tartrate].12H₂O (0.26 g, 0.2 mmol) and IPBP (0.210 g, 0.56 mmol) was dissolved in the mixture solution combined by glycol and water, and the solution was refluxed for 6 h. Then the reaction solution was cooled to room temperature, filtrated and diluted by water (40 mL), and saturation NH₄PF₆ solution was added to give an orange precipitation. The mixture was filtrated extraction, and the precipitate was washed by water ether and dried in vacuum. The crude product was dissolved in CH₃CN (5 mL), purified by Al₂O₃ column using CH₃CN—C₆H₅CH₃ solution as elute, and the main red composite was collected, dried in vacuum, re-crystal from CH₃CN—C₆H₅CH₃ solution to give red crystal, yield, 72%. ESI-MS (m/e): 937.0; 791.3; 396.27. CD (in Tris-HCl, pH=7.2, $\lambda_{max}$): +291.0 nm.

Example 5

Preparation of Δ-[Ru(bpy)₂(IPBH)](PF₆)₂(Δ-3)

The synthesized route of Δ-[Ru(bpy)₂(IPBH)](PF₆)₂(Δ-3) is show in figure (V):

(V)

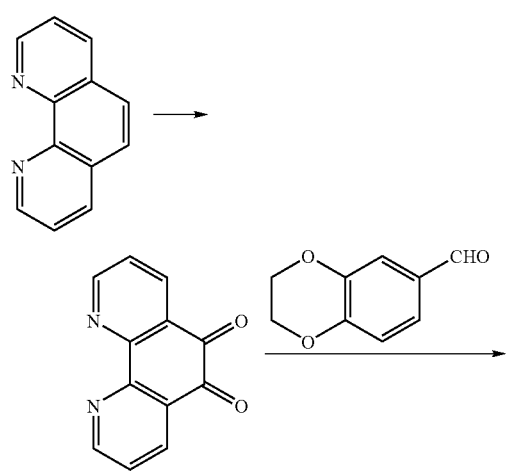

Phenanthroline dione-5,6, cis-[Ru(bpy)₂Cl₂], cis-[Ru(bpy)₂(py)₂]Cl₂ and Δ-[Ru(bpy)₂(py)₂][O,O'-dibenzoyl-d-tartrate].12H₂O was synthesized according the same procedure as that in example 1.

5.1 Preparation of 2-(1,4-benzodioxan) imidazole [4,5-f][1,10]phenanthroline (IPBH)

Phenanthroline dione-5,6 (0.315 g, 1.5 mmol) and 1,4-benzodioxan-6-carboxaldehyde (0.246 g, 1.5 mmol), ammonium acetate (2.31 g, 30 mmol) and glacial acetic acid (20 ml) refluxed for 2 h with stir, cooled to room temperature and diluted by water (80 mL). Then the pH of the solution was adjusted to nearly neuter by adding ammonia, and the solution was extracted with chloroform (20 mL) for 3 times. The brown-yellow crude product was obtained by filtrated the solution under extracted pressure and dried in vacuum. The crude product was re-crystal in ethanol, yield, 67.1%.

5.2 Preparation of Δ-[Ru(bpy)₂(IPBH)](PF₆)₂ (Δ-3)

Δ-[Ru(bpy)₂(py)₂][O,O'-dibenzoyl-d-tartrate].12H₂O (0.13 g, 0.1 mmol) and IPBH (0.107 g, 0.3 mmol) was dissolved in the mixture solution combined by glycol and water, and the solution was refluxed for 6 h. Then the reaction solution was cooled to room temperature, filtrated and diluted by water (40 mL), and saturation NH₄PF₆ solution was added to give an orange precipitation. The mixture was filtrated extraction, and the precipitate was washed by water ether and dried in vacuum. The crude product was dissolved in CH₃CN (5 mL), purified by Al₂O₃ column using CH₃CN—C₆H₅CH₃ solution as elute, and the main red composite was collected, dried in vacuum, re-crystal from CH₃CN—C₆H₅CH₃ solution to give red-yellow crystal, yield, 74%. ESI-MS (m/e): 913.0; 767.2; 384.3. CD (in Tris-HCl, pH=7.2, $\lambda_{max}$): −292.0 nm.

Example 6

Preparation of Λ-[Ru(bpy)₂(IPBH)](PF₆)₂ (Λ-3)

The synthesized route of Λ-[Ru(bpy)₂(IPBH)](PF₆)₂(Λ-3) was show in Figure (VI):

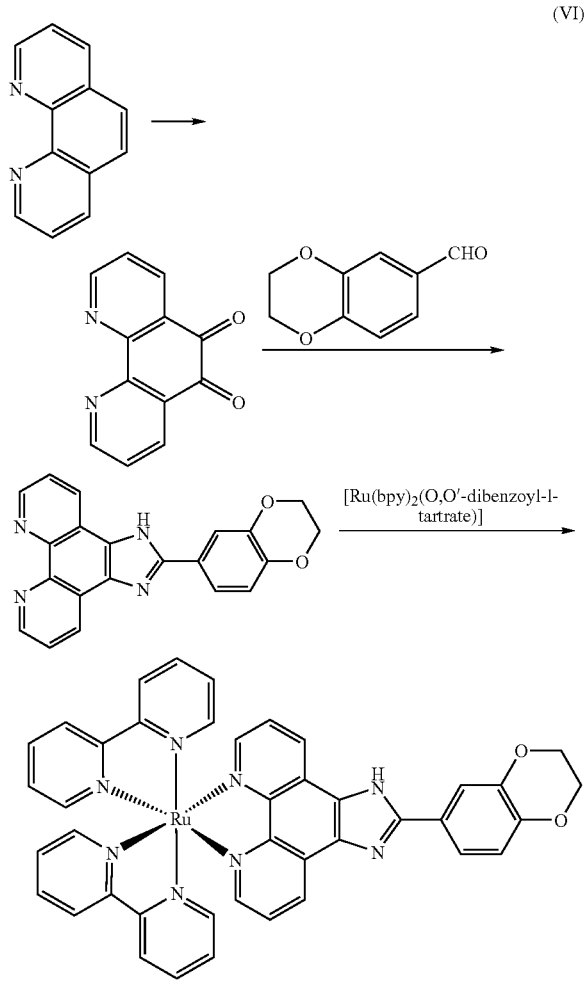

Phenanthroline dione-5,6, cis-[Ru(bpy)₂Cl₂] and cis-[Ru (bpy)₂ (py)₂]Cl₂ was synthesized according the same procedure as that in example 1. [Ru(bpy)₂(bpy)₂][O,O'-dibenzoyl-1-tartrate].12H₂O was synthesized according the same procedure as that in example 2. IPBP was synthesized according the same procedure as that in example 5.

Λ-[Ru(bpy)₂(bpy)₂][O,O'-dibenzoyl-1-tartrate].12H₂O (0.13 g, 0.1 mmol) and IPBP (0.107 g, 0.3 mmol) was dissolved in the mixture solution combined by glycol and water, and the solution was refluxed for 6 h. Then the reaction solution was cooled to room temperature, filtrated and diluted by water (40 mL), and saturation NH₄PF₆ solution was added to give an orange precipitation. The mixture was filtrated extraction, and the precipitate was washed by water ether and dried in vacuum. The crude product was dissolved in CH₃CN (5 mL), purified by Al₂O₃ column using CH₃CN—C₆H₅CH₃ solution as elute, and the main red composite was collected, dried in vacuum, re-crystal from CH₃CN—C₆H₅CH₃ solution to give red crystal, yield, 76%. ESI-MS (m/e): 912.87; 767.3; 384.3. CD (in Tris-HCl, pH=7.2, $\lambda_{max}$): 292.0 nm.

Example 7

Preparation of Δ-[Ru(bpy)₂(PYNI)](PF₆)₂ (Δ-4)

The synthesized route of Δ-[Ru(bpy)₂(PYNI)](PF₆)₂ (Δ-4) was show in figure (VII).

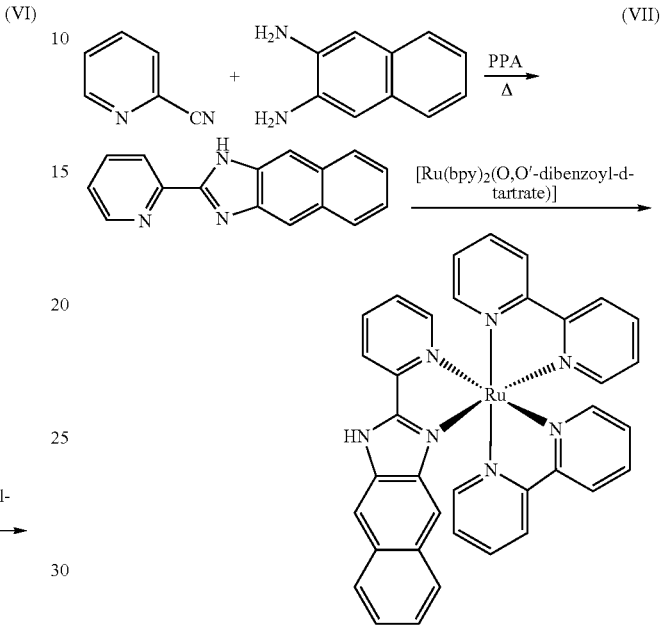

Phenanthroline dione-5,6, cis-[Ru(bpy)₂Cl₂], cis-[Ru (bpy)₂ (py)₂]Cl₂ and Δ-[Ru(bpy)₂(py)₂][O,O'-dibenzoyl-d-tartrate].12H₂O was synthesized according the same procedure as that in example 1.

7.1 Preparation of PYNI 2-cyno-pyridine (0.312 g, 3 mmol), 2,3-diaminonaphthalene (0.246 g, 1.5 mmol) and PPA (6 ml) was refluxed for 6 h at 175° C., and the reaction mixture was poured into water (50 ml) swiftly as the temperature of solution was cooled to 80° C., neutralized by 25% ammonia solution, and brown-green precipitate was obtained. The crude product was re-crystal in ethanol, dried in vacuum to give brown-green powder, yield, 76.2%.

7.2 Preparation of Δ-[Ru(bpy)₂(PYNI)](PF₆)₂ (Δ-4)

Δ-[Ru(bpy)₂(bpy)₂][O,O'-dibenzoyl-d-tartrate].12H₂O (0.13 g, 0.1 mmol) and PYNI (0.0735 g, 0.3 mmol) was dissolved in the mixture solution combined by glycol and water, and the solution was refluxed for 6 h. Then the reaction solution was cooled to room temperature, filtrated, and diluted by water (40 mL), and saturation NH₄PF₆ solution was added to give an orange precipitation. The mixture was filtrated extraction, and the precipitate was washed by water ether and dried in vacuum. The crude product was dissolved in CH₃CN (5 mL), purified by Al₂O₃ column using CH₃CN—C₆H₅CH₃ solution as elute, and the main red composite was collected, dried in vacuum, re-crystal from CH₃CN—C₆H₅CH₃ solution to give brown crystal, yield, 80%. ESI-MS (m/e): 658.2; 583.9; 329.7. CD (in Tris-HCl, pH=7.2, $\lambda_{max}$): −294 nm.

Example 8

Preparation of Λ-[Ru(bpy)$_2$(PYNI)](PF$_6$)$_2$ (Λ-4)

The synthesized of Λ-[Ru(bpy)$_2$(PYNI)](PF$_6$)$_2$ (Λ-4) was shown in figure (VIII).

Phenanthroline dione-5,6, cis-[Ru(bpy)$_2$Cl$_2$] and cis-[Ru(bpy)$_2$(py)$_2$]Cl$_2$ was synthesized according the same procedure as that in example 1. [Ru(bpy)$_2$(bpy)$_2$][O,O'-dibenzoyl-1-tartrate].12H$_2$O was synthesized according the same procedure as that in example 2. PYNI was synthesized according the same procedure as that in example 7.

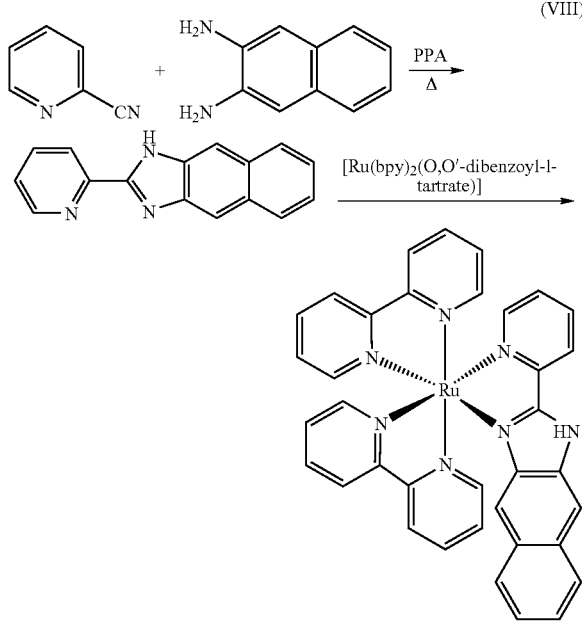

(VIII)

Δ-[Ru(bpy)$_2$(py)$_2$][O,O'-dibenzoyl-1-tartrate].12H$_2$O (0.13 g, 0.1 mmol) and PYNI (0.0735 g, 0.3 mmol) was dissolved in the mixture solution combined by glycol and water, and the solution was refluxed for 6 h. Then the reaction solution was cooled to room temperature, filtrated, and diluted by water (40 mL), and saturation NH$_4$PF$_6$ solution was added to give an orange precipitation. The mixture was filtrated extraction, and the precipitate was washed by water ether and dried in vacuum. The crude product was dissolved in CH$_3$CN (5 mL), purified by Al$_2$O$_3$ column using CH$_3$CN—C$_6$H$_5$CH$_3$ solution as elute, and the main red composite was collected, dried in vacuum, re-crystal from CH$_3$CN—C$_6$H$_5$CH$_3$ solution to give brown crystal, yield, 79%. ESI-MS (m/e): 658.2; 583.8; 329.8. CD (in Tris-HCl, pH=7.2, $\lambda_{max}$): +294 nm.

Example 9

Inhibitory Activity Against the Growth of Cancer Cells of Ruthenium Complexes The inhibitory activity of these chair ruthenium(II) complexes have been evaluated by MTT assay by using 5-fluorouracil (5-Fu) as positive control. Human hepatocarcinoma cell line Bel-7402, human intestinal adenocarcinoma cell line HCT-8 and Human lung adenocarcinoma epithelial cell line A-549 were supplied by the Institute of Materia Medica, Chinese Academy of Medical Sciences & Peking Union Medical College. The determination of the cytotoxicity (dark toxicity) of the compound was carried out in parallel with the phototoxicity determination following the same procedure, with the exclusion of the irradiation.

General method: Cells were diluted to 5000/ml by PRMI1640 minimal essential medium with 10% fetal calf serum (FCS), plated at 100 μl cells per well in a 96-well Corning microtiter plate, and incubated at 37° C. with 5% CO$_2$ for 24 h. After cell was covered a single layer, drugs (10 μl) was added, and PRMI1640 minimal essential medium was supplied to make the total volume to 200 μl. After incubated for another 72 h at 37° C., 5% CO$_2$, the medium was removed and freshly prepared MTT dissolved in DMSO (200 μl) was added, and the OD value was recorded on ELISA Reader at 544 nm. The inhibitory activity of ruthenium complexes was calculated according to equation:

$$\text{Inhibitory activity}(\%) = (OD_{blank} - OD_{sample}) / (OD_{control} - OD_{blank}) \times 100\%.$$

The inhibitory activity (%) of ruthenium complexes against human hepatocarcinoma cell Bel-7402, human intestinal adenocarcinoma cell HCT-8 and human lung adenocarcinoma epithelial cell A-549 was list table 1.

TABLE 1

Inhibitory activity of chair ruthenium(II) complexes against BEL-7402, HCT-8 and A-549 tumor cell line

| Complex | Dosage (μg/ml) | Inhibitory activity (%) BEL-7402 | HCT-8 | A-549 |
|---|---|---|---|---|
| Δ-1 | 5 | 85.0 | 81.6 | 62.0 |
|  | 50 | 88.3 | 86.2 | — |
| Λ-1 | 5 | 85.2 | 83.0 | 56.4 |
|  | 50 | 88.8 | 88.9 | — |
| Δ-2 | 5 | 9.6 | 13.1 | 18.5 |
|  | 50 | 86.8 | 83.4 | — |
| Λ-2 | 5 | 0.19 | 2.23 | −0.52 |
|  | 50 | 64.9 | 53.7 | — |
| Δ-3 | 5 | — | — | — |
|  | 50 | — | — | — |
| Λ-3 | 5 | 3.0 | 2.1 | −0.92 |
|  | 50 | 44.3 | 39.1 | — |
| Δ-4 | 5 | 2.8 | 1.8 | −8.2 |
|  | 50 | 36.0 | 38.6 | — |
| Λ-4 | 5 | 4.4 | 3.6 | −2.3 |
|  | 50 | 22.6 | 21.4 | — |
| 5-FU | 5 | 81.8 | 76.3 | 82.3 |
|  | 50 | 77.1 | 86.4 | — |

It's show in table 1 that all of these chair ruthenium(II) complexes exhibit excellent antitumor activity against human hepatocarcinoma cell Bel-7402 and human intestinal adenocarcinoma cell HCT-8 at high drug dosage (50 μg/ml), especially Δ-1(88.3%; 86.2%); Λ-1(88.8%; 88.9%); Δ-2(86.8%; 83.4%) and Λ-2(64.9%; 53.7%). At low drug dosage (5 μg/ml), ruthenium(II) complexes Δ/Λ-[Ru(bpy)$_2$(FPIP)]$^{2+}$ exhibit higher inhibitory activity against BEL-7402, HCT-8 and A-549 cells than that of positive control of 5-Fu. Under our experiment condition, all ruthenium(II) complexes, especially left-hand enantiomer, exhibit higher inhibitory activity against human hepatocarcinoma cell Bel-7402 than that of HCT-8 and A-549 cells.

The invention claimed is:

1. A chair ruthenium complex represented by the general formula of A-[Ru(bpy)$_2$L](PF$_6$)$_2$, where A is Δ or Λ; L is 2-(2-trifluoromethane phenyl)imidazole[4,5-f][1,10]phenanthroline (tFPIP), 2-(4-methyl-1,2-benzopyriran-2- one)imidazole[4,5-f][1,10]phenanthroline (IPBP), or 2-(1,4-benzodioxan)imidazole[4,5-f][1,10]-phenanthroline (IPBH).

2. The chair ruthenium complex according to claim 1, wherein the complex is selected from the group consisting of Δ-[Ru(bpy)$_2$(tFPIP)](PF$_6$)$_2$, Λ-[Ru(bpy)$_2$(tFPIP)](PF$_6$)$_2$, Δ-[Ru(bpy)$_2$(IPBP)](PF$_6$)$_2$, Λ-[Ru(bpy)$_2$(IPBP)](PF$_6$)$_2$, Δ-[Ru(bpy)$_2$(IPBH)](PF$_6$)$_2$, and Λ-[Ru(bpy)$_2$(IPBH)](PF$_6$)$_2$.

3. A pharmaceutical composition comprising as an active ingredient at least one chair ruthenium complex according to claim 1.

4. A method for treating hepatocarcinoma comprising administrating to a subject in need of such treatment, an effective amount of at least one chair ruthenium complex according to claim 1.

5. A method for treating intestinal adenocarcinoma comprising administrating to a subject in need of such treatment, an effective amount of at least one chair ruthenium complex according to claim 1.

* * * * *